(12) United States Patent
Cramer et al.

(10) Patent No.: US 6,239,262 B1
(45) Date of Patent: May 29, 2001

(54) LOW MOLECULAR WEIGHT DISPLACERS FOR PROTEIN PURIFICATION IN HYDROPHOBIC INTERACTION AND REVERSED PHASE CHROMATOGRAPHIC SYSTEMS

(75) Inventors: Steven M. Cramer, Schenectady, NY (US); Abhinav A. Shukla, Bothell, WA (US); Khurram M. Sunasara, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 09/223,093

(22) Filed: Dec. 30, 1998

Related U.S. Application Data

(60) Provisional application No. 60/070,653, filed on Jan. 7, 1998.

(51) Int. Cl.[7] .............................. C07K 1/14; B01D 15/08
(52) U.S. Cl. ..................... 530/417; 530/413; 530/416; 530/427; 210/198.2; 210/635; 210/656
(58) Field of Search ................................... 530/417, 413, 530/416, 427; 210/198.2, 635, 656

(56) References Cited

U.S. PATENT DOCUMENTS

| | | | |
|---|---|---|---|
| 5,043,423 | 8/1991 | Viscomi et al. | 530/344 |
| 5,427,686 | 6/1995 | Asher | 210/635 |
| 5,439,591 | 8/1995 | Piura et al. | 210/635 |
| 5,478,924 | * 12/1995 | Cramer et al. | 530/416 |
| 5,606,033 | 2/1997 | Cramer et al. | 530/416 |

OTHER PUBLICATIONS

Antia et al., *Ind. Eng. Chem. Res.,* vol. 34, No. 8, pp. 2796–2804, 1995.*
"Hiload™ Phenyl Sephause® High Performance," Data File, Pharmacia Biotech. (18–1022–55).*
Visconni et al., *Journal of Chromotography,* vol. 549, pp. 175–184, 1991.*
Sofer et al., *Bio Techniques,* vol. 1, No. 4, pp. 198–203, 1983.*
Bonneyer et al., *Bio Technology,* vol. 4, pp. 954–958, Nov. 1986.*

Schneich et al., *Anal. Chem.,* vol. 65, pp. 67R–84R, 1993.*
Jayaraman et al., *Journal of Chromatography A,* vol. 702, pp. 143–155, 1995.*
Kundu et al., Biotechnology abd Bioengineering, vol. 48, No. 5, pp. 452–460, 1995.*
Kundu et al., *BioPharm,* vol. 10, No. 5, pp. 64–70, May 1997.*
Kundu et al., *Molytical Biochemistry,* vol. 248, pp. 111–116, 1997.*
Kundu et al., *Biotechnology and Bioengineering,* vol. 56, No. 2, pp. 119–129, 1997.*
Barnthouse et al., *Journal of Biotechnology,* vol. 66, No. 2–3, pp. 125–136, 1998.*
S. Rose *Protein Purification Methods, a Practical Approach,* Chapter 4, pp. 230–232, 1989.*
"Displacement of Proteins in Hydrophobic Interaction Chromatography", Antia et al., Ind. Eng. Chem. Res., 34, 2796–2804, (1995).
"Protected amino acids as novel low molecular weight displacers in cation–exchange chromatography", Kundu et al., Biotechnol. Bioeng., 48, 452–460, (1995).
"High Performance Displacement Chromatography", Frenz et al., HPLC–Advances and Perspectives vol. 5, Hy Cs. Horvath (ed.), Academic Press, (1988).
"Displacement Chromatography in Peptide Purification", Cramer et al., Preparative Chromatography, 1, 29–49, (1988).
"Reversed phase and Hydrophobic Interaction Chromatography of peptides and proteins", Rassi et al., Separation processes in Biotechnology by J.A. Asenjo (ed.), Marcel Dekker, (1990).
"Protein separation by hydorphobic interaction chromatography using methacrylic block copolymers as displacers", Ruaan et al., Journal of Chromatography A, pp. 35–43, (1998).

* cited by examiner

*Primary Examiner*—Christopher S. F. Low
*Assistant Examiner*—Abdel A. Mohamed
(74) *Attorney, Agent, or Firm*—Heslin & Rothenberg, PC

(57) ABSTRACT

A method for purification of proteins by displacement chromatography in hydrophobic interaction and reversed phase chromatographic systems uses low molecular weight (less than about 10,000) surface-active compounds as displacers. Examples of effective displacers are benzethonium chloride, benzyltributylammonium chloride, and tetrahexylammonium chloride.

31 Claims, 18 Drawing Sheets

LOW MOLECULAR WEIGHT DISPLACERS FOR PROTEIN PURIFICATION IN HYDROPHOBIC INTERACTION AND REVERSED PHASE CHROMATOGRAPHIC SYSTEMS

This appln claims the benefit of Provisional No. 60/070,653 filed Jan. 7, 1998.

FIELD OF THE INVENTION

The invention relates to displacement chromatography of proteins in hydrophobic interaction and reversed phase liquid chromatographic systems using low molecular weight, surface active-compounds as displacers.

BACKGROUND OF THE INVENTION

Proteins have become commercially important as drug candidates and in other therapeutic applications. One of the greatest challenges is the development of cost effective and efficient processes for purification of proteins on a commercial scale. While many methods are now available for large scale preparation of proteins, crude products contain not only the desired product but also closely related impurities which are difficult to separate from the desired product. Moreover, biological sources of proteins usually produce complex mixtures of materials.

The term "protein" as commonly understood in the art, and as used herein, refers to peptides having a molecular weight of 10,000 or greater. Peptides having a molecular weight of less than 10,000 are known as polypeptides.

Ion exchange systems chromatographic systems have been used widely for separation of proteins primarily on the basis of differences in charge. Chromatographic systems having a hydrophobic stationary phase offer an alternative basis for separations and have also been widely employed in the purification of proteins. Included in this category are hydrophobic interaction chromatography (HIC) and reversed phase liquid chromatography (RPLC). The physicochemical basis for separation by HIC and RPLC is the hydrophobic effect; proteins are separated on a hydrophobic stationary phase based on differences in hydrophobicity.

Although both HIC and RPLC utilize a hydrophobic stationary phase, the composition of the surface of the hydrophobic or non-polar stationary phase differs. Materials used as a stationary phase in RPLC have what can be considered a "hard" hydrophobic surface, characterized by high interfacial tension between the surface and an aqueous mobile phase. In contrast, the surface of the stationary phase in HIC is composed of a hydrophilic organic layer having weakly non-polar groups attached. This is termed a "soft" surface. In addition, the surface density of hydrophobic groups is generally higher in RPLC systems Man in HIC.

The different surface characteristics of the two systems mandate the use of different mobile phases so that the interaction between the solute and the stationary phase results in a retention time which falls within the range of practical values for the separation. Thus, the mobile phases employed in HIC are typically aqueous with high salt concentrations; most proteins have a higher retention at higher salt concentration. Those used in RPLC are aqueous with organic modifiers, such as acetonitrile and methanol; most proteins have lower retention with higher organic modifier concentrations.

A chromatographic system can be operated in one of two major modes, elution (including linear gradient, step gradient, and isocratic elution) or displacement. The two modes may be distinguished both in theory and in practice. In elution chromatography, a solution of the sample to be purified is applied to a stationary phase, commonly in a column. The mobile phase is chosen such that the sample is neither irreversibly adsorbed nor totally unadsorbed, but rather binds reversibly. As the mobile phase is flowed over the stationary phase, an equilibrium is established between the mobile phase and the stationary phase whereby, depending on the affinity for the stationary phase, the sample passes along the column at a speed which reflects its affinity relative to the other components that may occur in the original sample. The differential migration process is outlined schematically in FIG. 1, and a typical chromatogram is shown in FIG. 2. Of particular note is the fact that the eluting solvent front, or zero column volume in isocratic elution, always precedes the sample off the column.

A modification and extension of isocratic elution chromatography is found in step gradient chromatography wherein a series of eluants of varying composition is passed over the stationary phase. In reversed phase chromatography, step changes in the mobile phase modifier concentration (e.g., acetonitrile) are employed to elute or desorb the proteins.

A schematic illustrating the operation of a chromatographic system in displacement mode is shown in FIG. 3. The column is initially equilibrated with a buffer in which most of the components to be separated have a relatively high affinity for the stationary phase. Following the equilibration step, a feed mixture containing the components to be separated is introduced into the column and is then followed by a constant infusion of the displacer solution. A displacer is selected such that it has a higher affinity for the stationary phase than any of the feed components. As a result, the displacer can effectively drive the feed components off the column ahead of its front. Under appropriate conditions, the displacer induces the feed components to develop into adjacent "squarewave" zones of highly concentrated pure material. The displacer emerges from the column following the zones of purified components. After the breakthrough of the displacer with the column effluent, the column is regenerated and is ready for another cycle.

An important distinction between displacement chromatography and elution chromatography is that in elution chromatography, desorbents, including for reversed phase chromatography, organic mobile phase modifiers such as acetonitrile, move through the feed zones, while in displacement chromatography, the displacer front always remains behind the adjacent feed zones in the displacement train. This distinction is important because relatively large separation factors are generally required to give satisfactory resolution in elution chromatography, while displacement chromatography can potentially purify components from mixtures having low separation factors. The key operational feature which distinguishes displacement chromatography from elution chromatography is the use of a displacer molecule. In elution chromatography, the eluant usually has a lower affinity for the stationary phase than do any of the components in the mixture to be separated, whereas, in displacement chromatography, the eluant, which is the displacer, has a higher affinity.

Displacement chromatography has some particularly advantageous characteristics for process scale chromatography of biological macromolecules such as proteins. First, displacement chromatography can concentrate components from mixtures. By comparison, isocratic elution chromatography results in product dilution during separation. Second, displacement chromatography can achieve product separation and concentration in a single step. Third, since the displacement process operates in the nonlinear region of the equilibrium isotherm, high column loadings are possible. This allows much better column utilization than elution chromatography. Fourth, displacement chromatography can purify components from mixtures having low separation factors, while relatively large separation factors are required for satisfactory resolution in desorption chromatography.

Preparative chromatography operated in the displacement mode is therefore a potentially attractive method for purifying proteins because of the high resolution and high throughput obtainable. However, the use of high molecular weight displacers has been a deterrent to the implementation of this technology. In contrast, low molecular weight displacers have significant operational advantages as compared to large molecular weight displacers. First and foremost, if there is any overlap between the displacer and the protein of interest, these low molecular weight materials can be readily separated from the purified protein after the displacement process using size-based purification methods, e.g., size exclusion chromatography or ultrafiltration. Furthermore, the relatively low cost of low molecular weight displacers can be expected to significantly improve the economics of displacement chromatography. It is also likely that column regeneration with these materials will require less extreme conditions and reduced regenerant volumes. Additional potential advantages include the rapid mass transport of these small displacers and the ability to carry out selective displacement chromatography where the displacer selectively displaces a bioproduct of interest while desorbing the higher affinity impurities.

Prior art disclosures relating to purification of proteins by hydrophobic interaction chromatography or reversed phase liquid chromatography have described only the use of relatively large molecules (>40,000 Daltons) as displacers. For example, Antia et al. have employed high molecular weight proteins in HIC as displacers for proteins. This methodology suffers from several disadvantages, including contamination of the purified product with the protein used as the displacer, the need to validate the removal of biologically active materials prior to FDA approval of a process, and the high costs associated with using a protein as a displacer. It is not clear from the prior art that one could displace a protein in a hydrophobic interaction chromatographic system with a low molecular weight compound. While displacers have been successful in separating peptides on reversed phase media, before the present invention, no one had reported success in the displacement chromatography of proteins in RPLC with any class of displacers.

In considering potential displacers for use in HIC or RPLC, an important constraint arises from the need to preserve the bioactivity of the protein. Many conditions and displacers that one might be tempted to extrapolate from the chromatography of peptides will be inappropriate for proteins because they will denature the product sought to be purified. Thus, it is not clear from the prior art that one could displace a protein in either a HIC or RPLC system using low molecular weight displacers.

Therefore, there is a need for a separation process for proteins having the advantages of displacement chromatography, combined with the advantages of low molecular weight displacers, that is, high resolution and high throughput, combined with facile column regeneration and facile removal of displacer from the product.

SUMMARY OF THE INVENTION

The method of the present invention fulfills these needs.

In one aspect, the invention relates to a method for purifying a protein, or several proteins, comprising (a) configuring a chromatographic system having a hydrophobic stationary phase for operation in displacement mode; (b) selecting a surface-active compound of molecular weight of less than about 10,000 for use as a displacer, (c) loading the protein on the hydrophobic stationary phase; and (d) displacing the protein from the stationary phase with the surface-active compound. A preferred molecular weight for the displacer is less than about 5,000; a more preferred molecular weight is less than about 2000.

A preferred chromatographic system is a hydrophobic interaction system. Another preferred chromatographic system is a reversed phase liquid chromatographic system.

A preferred surface-active compound has one or more alkyl, substituted alkyl, aromatic or substituted aromatic substituents. The surface-active compound may be anionic, cationic or nonionic. A preferred surface-active compound is chosen from the group consisting of: alkylaryl sulfonates, alkylaryl sulfonic acids, diphenyl sulfonate derivatives, quaternary amines, sulfonates of benzene, sulfonates of cumene, sulfonates of toluene, sulfonates of xylene, sulfonates of condensed naphthalene, sulfonates of dodecylbenzenes, sulfonates of tridecylbenzenes, sulfonates of naphthalene, sulfonates of alkyl naphthalene, tridecyl benzene sulfonic acids and dodecyl benzene sulfonic acids. Particularly preferred displacers are benzethonium chloride, benzyltributylammonium chloride, tetrahexylammonium chloride and rhodamine.

DETAILED DESCRIPTION OF THE INVENTION

Figure 1:
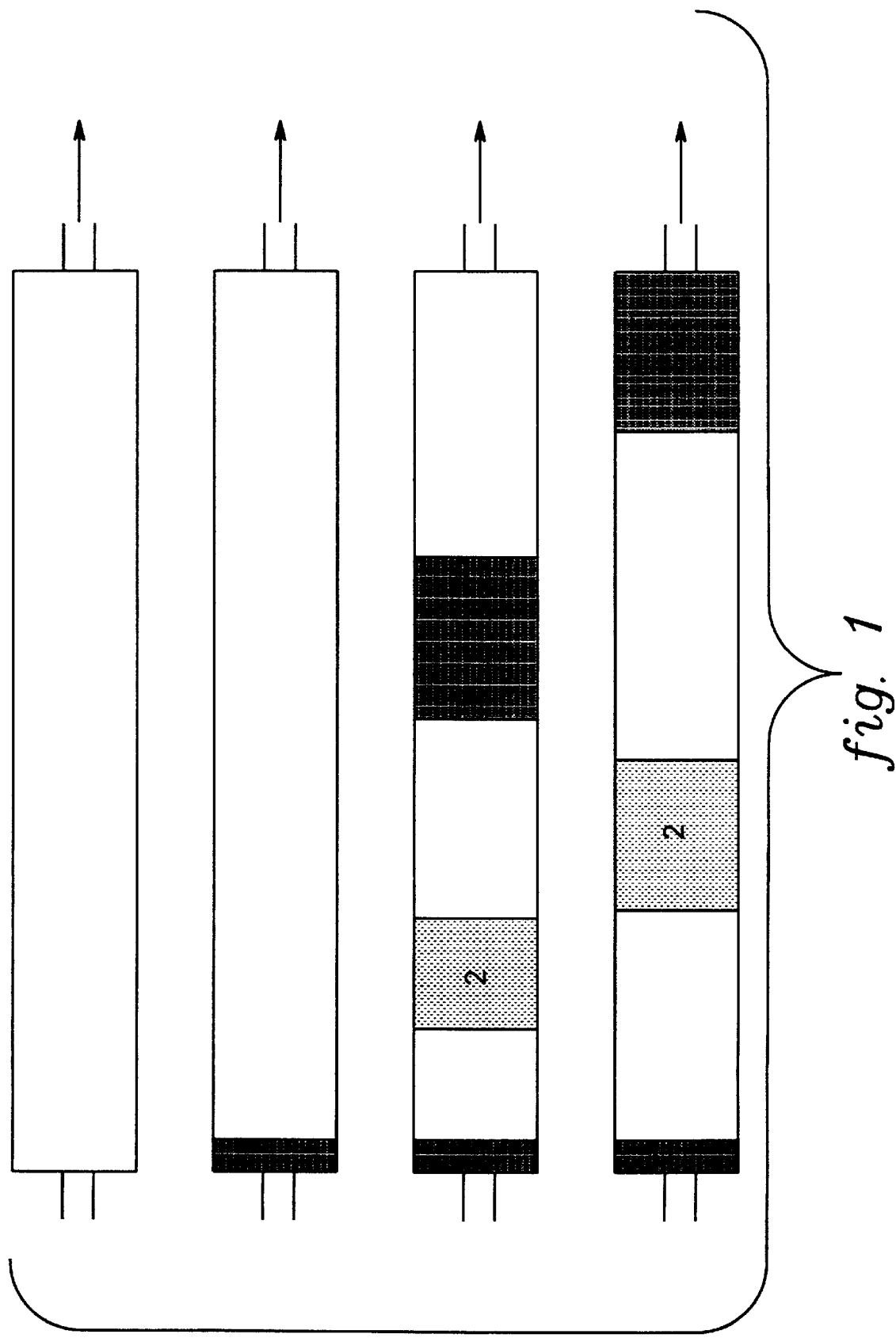
FIG. 1 is a schematic representation of isocratic linear elution chromatography as typically practiced.
Figure 2:
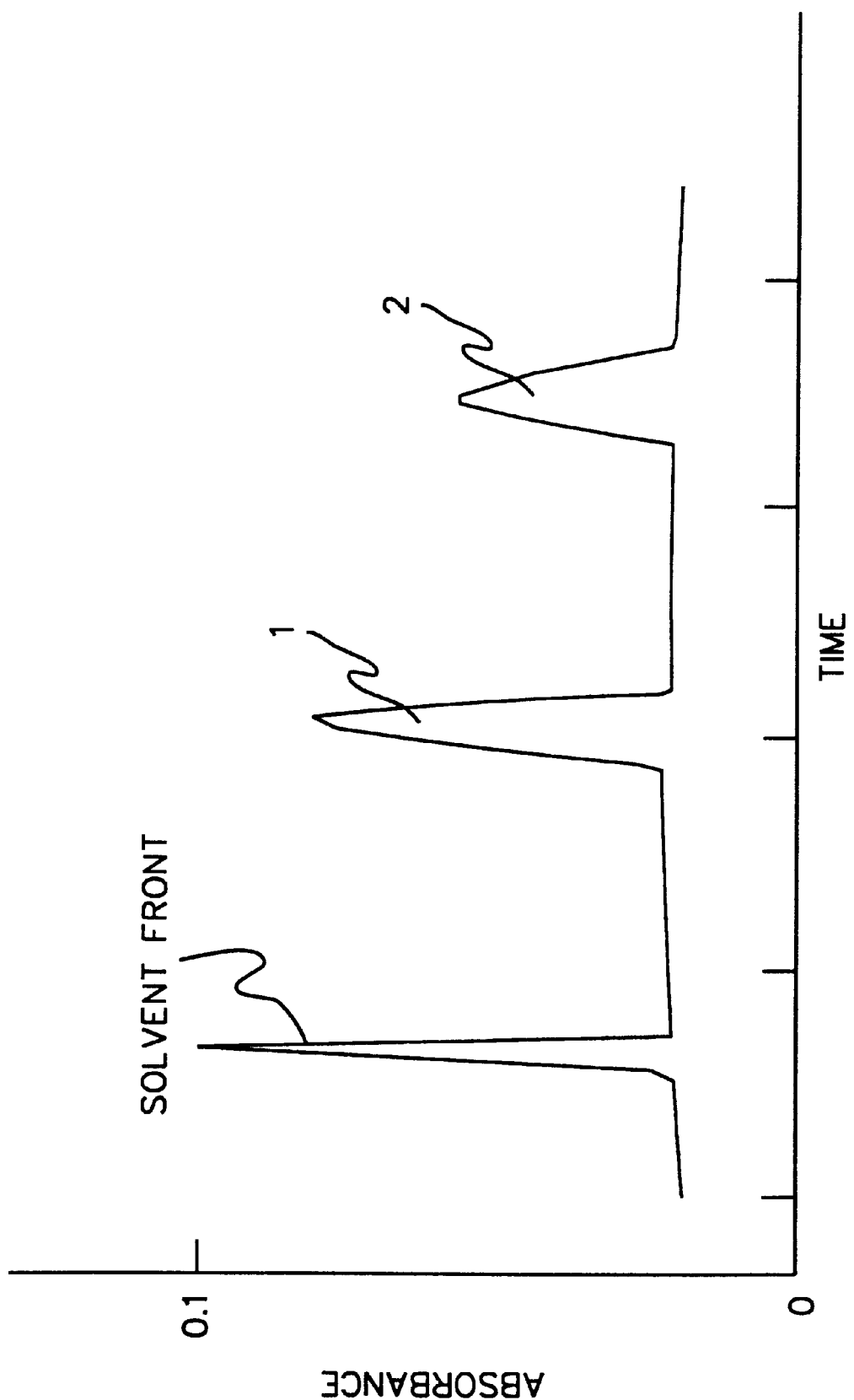
FIG. 2 is a typical elution chromatogram.
Figure 3:
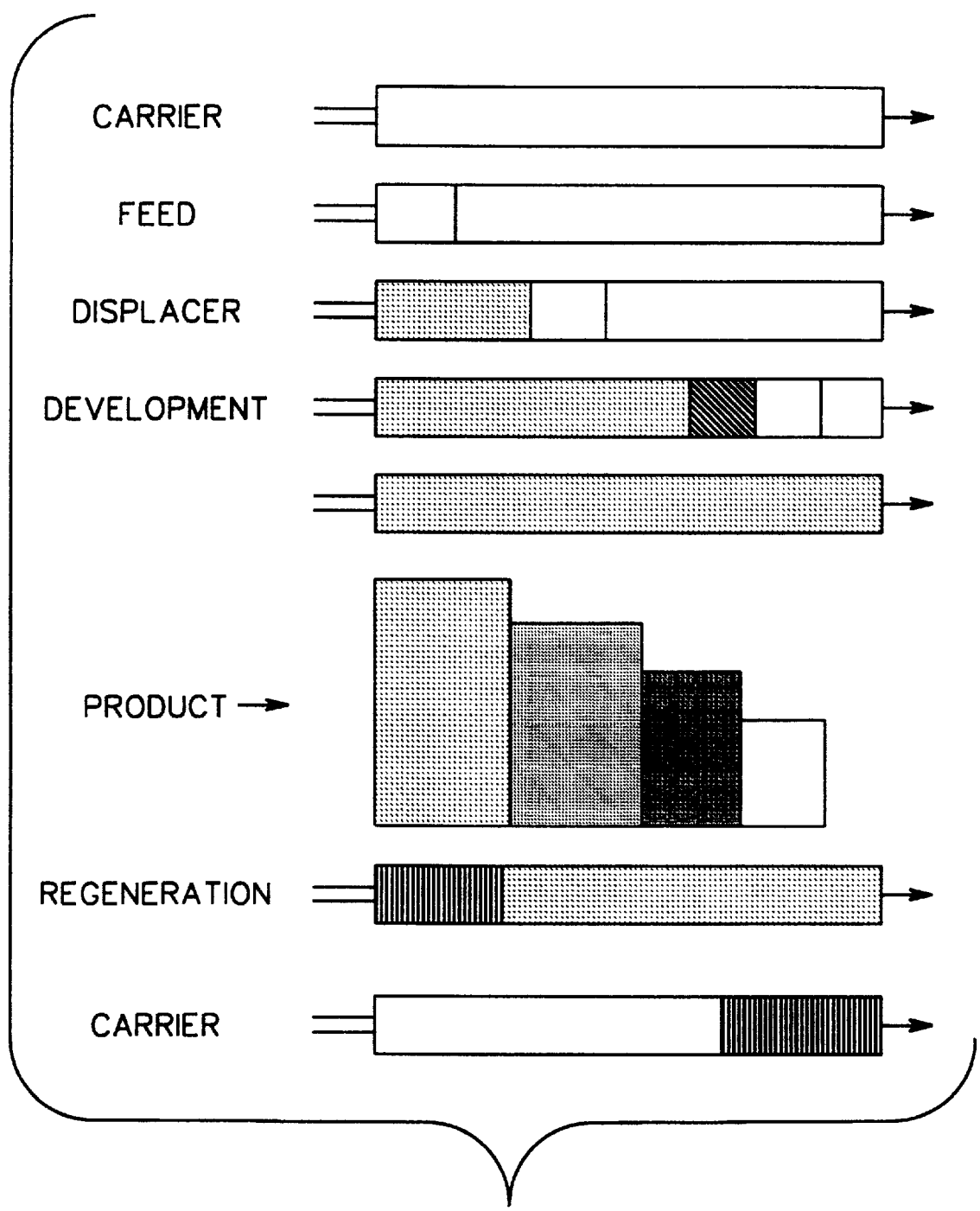
FIG. 3 is a schematic representation of displacement chromatography.

The method of the present invention relates to separation and purification of proteins by HIC and RPLC chromatography operated in the displacement mode. In particular, a surface-active compound having low molecular weight relative to compounds previously used as displacers for proteins in hydrophobic systems is used as a displacer.

The molecular weight of a displacer used in the method of the present invention should be less than about 10,000. Preferably, the molecular weight is less than about 5,000, and more preferably, the molecular weight is less than about 2000. Low molecular weight facilitates removal of the displacer from the product protein and from the stationary phase after the separation is completed.

"Surface-active compound" is defined herein as a molecule containing both hydrophilic and hydrophobic moieties or substituents. The hydrophilic part of the molecule is compatible with the aqueous environment of the mobile phase and promotes solubility of the displacer. The displacer should be sufficiently soluble in the mobile phase that solutions having concentrations of the displacer in the range conventionally used for displacement chromatography may be used, typically in the range of 1 mM to 100 mM. Examples of preferred hydrophilic substituents are sulfate, sulfonate, phosphate, phosphonate, carboxylate and quaternary ammonium groups. The hydrophobic part of the molecule promotes interaction of the displacer molecule with the hydrophobic surface and adsorption thereon. Examples of preferred hydrophobic substituents are aromatic, substituted aromatic, aliphatic and substituted aliphatic groups.

Conventional surfactants, including anionic, cationic and nonionic types, may be used as displacers. Surfactants of the following chemical classifications may be useful in the practice of the invention: alkanolamides, alkylaryl sulfonates, alkylaryl sulfonic acids, amine acetates, amine oxides, sulfonated amines and amides, betaine derivatives, block copolymers, carboxylated alcohol or alkylphenol ethoxylates, carboxylic acids/fatty acids, diphenyl sulfonate derivatives, ethoxylated alcohols, ethoxylated alkylphenols, ethoxylated amines and/or amides, glycerol esters, glycol esters, imidazolines and imidazoline derivatives, isethionates, phosphate esters, phosphorous organic derivatives, polyethylene glycols, propoxylated and ethoxylated fatty acids, alcohols, or alkyl phenols, quaternary amines, soaps, sulfates of alcohols, sulfates of ethoxylated alcohols, sulfonates of benzene, cumene, toluene, and xylene, sulfonates of condensed naphthalene, sulfonates of dodecyl and tridecylbenzenes, sulfonates of naphthalene and alkyl naphthalene, and tridecyl and dodecyl benzene sulfonic acids. Exemplary surfactant products and suppliers for each of the above-listed chemical classes are named in *McCutcheon's Volume* 1: *Emulsifiers and Detergents*, 1997 edition, published by MC Publishing Co., Glen Rock, N.J.

Preferred displacers are quaternary amines having alkyl chains shorter than eight carbons. Other preferred displacers are alkylaryl sulfonates, alkylaryl sulfonic acids, diphenyl sulfonate derivatives, quaternary amines, sulfonates of benzene, sulfonates of cumene, sulfonates of toluene, sulfonates of xylene, sulfonates of condensed naphthalene, sulfonates of dodecylbenzenes, sulfonates of tridecylbenzenes, sulfonates of naphthalene, sulfonates of alkyl naphthalene, tridecyl benzene sulfonic acids and dodecyl benzene sulfonic acids.

In addition to conventional surfactants, other surface-active compounds may be used as displacers. These include phase transfer catalysts, such as Aliquat 336, some dyes and other organic molecules containing both hydrophilic and hydrophobic moieties. Exemplary dyes useful in the practice of the invention are eosin B, eosin Y, rhodamine, CI natural orange 6, CI food orange 3, CI natural red 8 and CI natural yellow 10, available from Sigma-Aldrich. Particularly preferred surface-active organic compounds are benzethonium chloride, benzyltributyl ammonium chloride (BTBAC), and tetrahexylammonium chloride (THAC), available from Aldrich.

Surface-active compounds form micelles above a critical micelle concentration (CMC). In some cases, this can interfere with a separation. It is theorized that this interference results from the presence of a second hydrophobic phase that competes with the stationary phase for the protein. Therefore, in some cases, it may be desirable to use the surface-active compound at a concentration below the critical micelle concentration. It should be noted that the CMC is dependent on the concentration and type of cosolvent and the salt concentration. Specifically, the presence of cosolvents such as short-chain alcohols increases the CMC, while the presence of salts decreases the CMC.

In some cases, reversible or irreversible denaturation may result from interaction of a displacer molecule having alkyl substitutents greater than about seven or eight carbons in length. Under these conditions a surface-active compound having alkyl substituents about one to seven carbons in length, substituted alkyl about one to seven carbons in length, or aromatic or substituted aromatic groups may be used in order to minimize the possibility of denaturation of the protein being purified.

Ability of a particular surface-active compound to displace a particular protein may be predicted from linear retention data for the displacer and protein determined on the stationary phase to be used for the separation, and in solutions suitable as a mobile phase of varying concentrations. Typically, for a separation by HIC, a salt solution having a concentration ranging from 0.01 to 2 molal is used as the mobile phase. For a separation by RPLC, an aqueous solution of an organic modifier such as acetonitrile or methanol is typically used. An ion pairing agent such as trifluoracetic acid may also be included in a mobile phase for a separation by RPLC.

A series of elutions is performed, and retention times for the displacer and the protein at each concentration are recorded. For HIC, values for log (retention time) are plotted against salt concentration. For RPLC, values for log (retention time) are plotted against the concentration of organic modifier expressed as a volume percentage. A compound having a long retention time can generally displace one of shorter retention time. An effective displacer generally has a longer retention time than that of a protein to be separated at a range of mobile phase modifier concentrations. Therefore, on the plot, the line for the displacer should fall above that for the protein.

Figure 4:
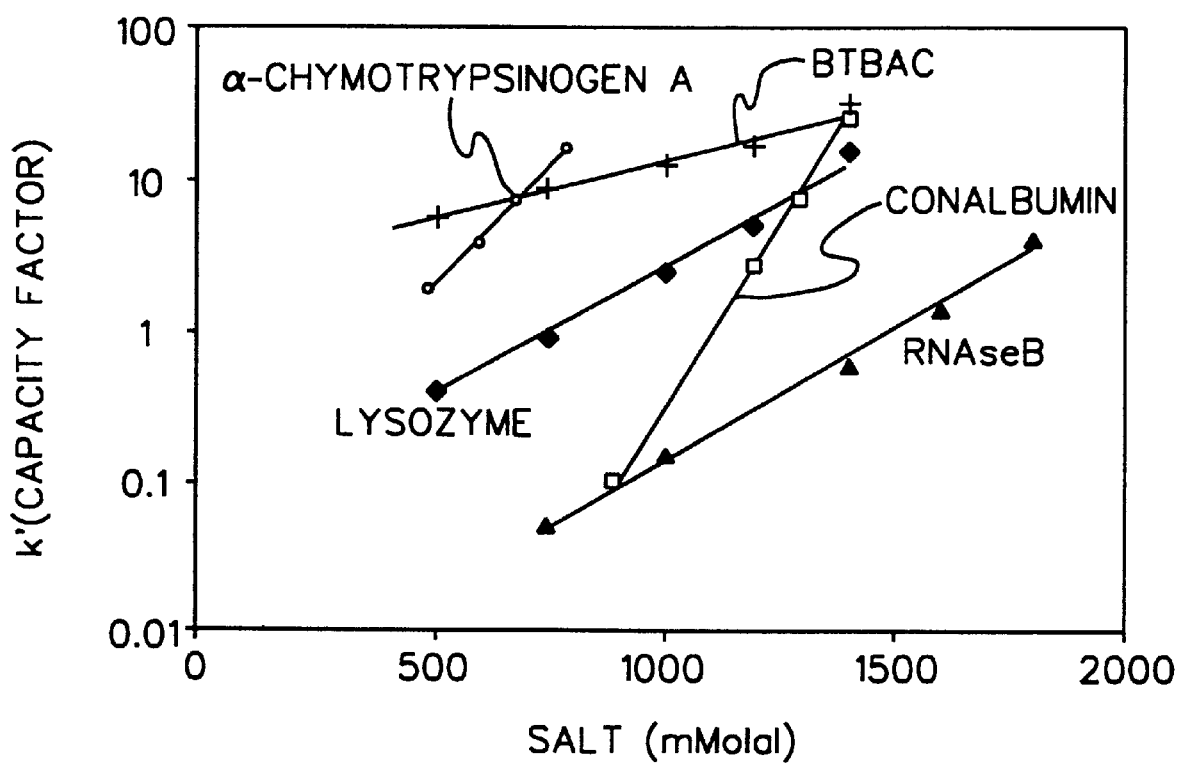
FIG. 4 is a plot of linear retention data obtained on a HIC system used for selection of a displacer.

An exemplary plot of log k' vs. salt concentration is shown in FIG. 4. For a separation by HIC, log k' is plotted against molal salt concentration for each of proteins lysozyme and conalbumin, and for displacer benzyltributyl ammonium chloride (BTBAC). The mobile phase is ammonium sulfate in a phosphate buffer. The plot shows the relative linear retention of the materials over a range of salt concentrations.

According to the figure, BTBAC has a higher k' than lysozyme, RNAseB, and conalbumin at salt concentrations below about 1.8 molal. Therefore, it should be capable of displacing these proteins below this salt concentration. BTBAC has a higher k' than α-chymotrypsinogen only below a concentration of about 0.75 molal, and is not expected to be able to displace it except at salt concentrations lower than that. These hypotheses were confirmed by displacement experiments.

A plot of log k' vs. molal salt concentration can provide useful insight into the choice of displacer as well as the mobile phase conditions under which a displacer may be employed; in most cases, it provides a rule of thumb for selecting a displacer for a particular separation problem. While a higher k' does not guarantee that a compound will be an effective displacer, in greater than 90% of cases, a compound having a higher k' than a protein to be separated at a particular range of salt concentrations will displace that protein under those conditions providing a sufficiently high concentration of displacer is employed.

Conventional HIC and RPLC hardware systems may be used for the separation, and the term "configuring a chromatographic system" refers to setting up a column or system of column, pump and detector as well known in the art. Exemplary materials useful as a stationary phase of a HIC system are the Phenyl 650M HIC Phenyl, Butyl and Ether series available from TosoHaas, Montgomeryville, Pa., and the Phenyl-, Butyl- and Octyl-Sepharose resins available from Amersham Pharmacia, Uppsala, Sweden. For a RPLC system, materials typically used as a stationary phase are the ZORBAX® series, including the C3, C4, C8 and C18 grades, from BTR Separations, Wilmington, Del.; Vydac C4, C8 and C18 RPLC columns from Vydac, Hesperia, Calif.; and Octadecyl Silica C18 and Phenyl and Octadecyl Resin Based columns, from TosoHaas.

Conventional displacement chromatography procedures may be applied to the separation. Displacement chromatography operations are typically carried out by initially equilibrating the column with carrier solution and then sequentially perfusing with feed, displacer, and regenerant solutions.

EXAMPLES

Separations by HIC

Example 1

Figure 5:
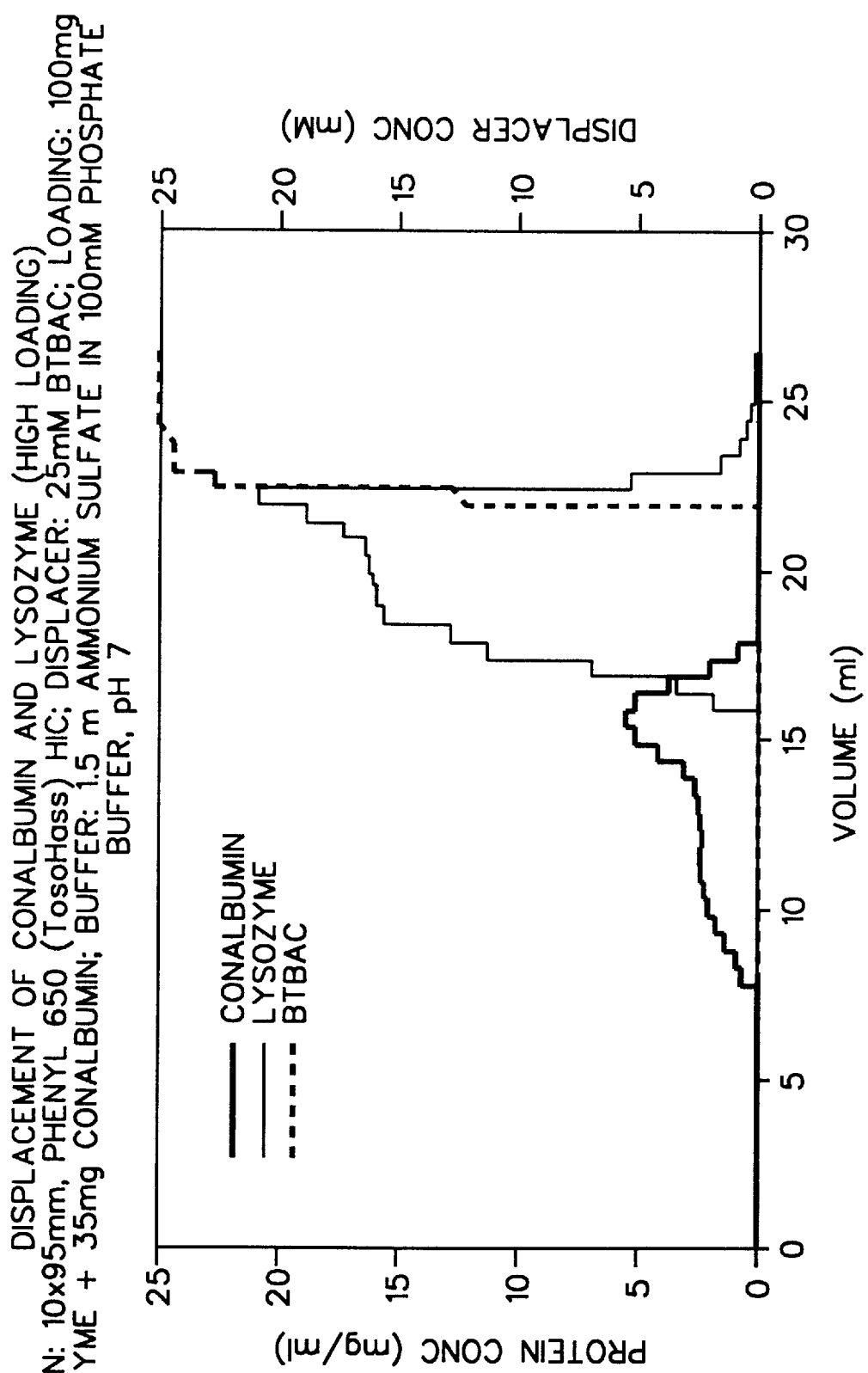
FIG. 5 is a displacement chromatogram for a typical protein mixture purified on a HIC column using a low molecular weight, surface-active compound of the present invention.

FIG. 5 shows a separation of two proteins, conalbumiin and lysozyme, on a Phenyl 650M (Toso Haas) HIC stationary phase using benzyltnrbutyl ammonium chloride (BTBAC) as a displacer. A separation was effected at a high protein loading (100 mg lysozyme and 35 mg conalbumin on a column having a volume of about 8 ml.)

It is significant that a protein as strongly bound as α-chymo-trypsinogen, a high affinity protein on the Phenyl 650M HIC stationary phase, was successfully displaced using a low molecular weight surface-active compound as a displacer. In addition, a comparison of the circular dichroism spectra of the proteins before and after purification by displacement chromatography showed no discernable changes. This indicates that protein displacement on HIC can be carried out using appropriate hydrophobic displacers without any detrimental effect on the secondary structure of the protein.

Separations by RPLC

Example 2

Figure 6:
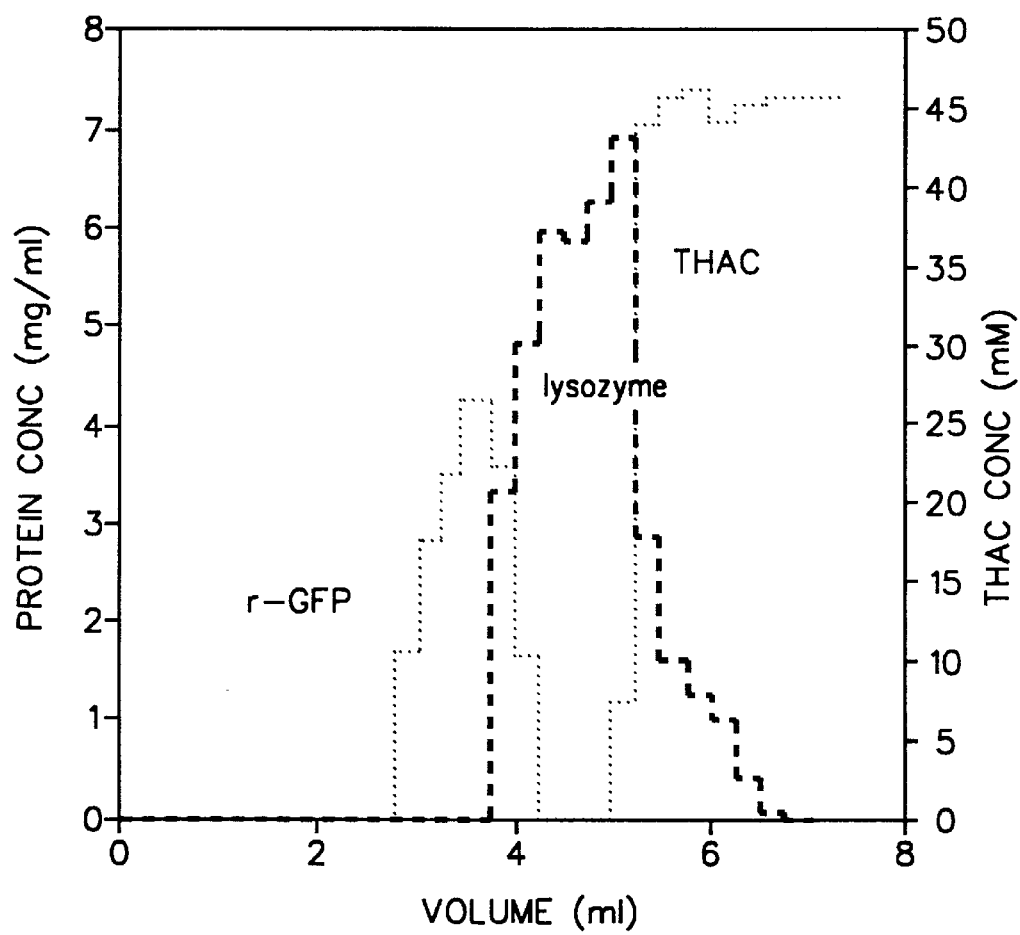
FIG. 6 is a displacement chromatogram for the purification of a typical protein mixture on a reversed phase column using a low molecular weight, surface-active compound of the present invention.

FIG. 6 shows a histogram from a displacement separation of proteins on reversed phase support using tetrahexylammonium chloride (THAC) as a displacer on a Vydac C4 column. (THAC had higher affinity on this stationary phase than BTBAC.) The carrier solution and mobile phase was a solution of 27% acetonitrile (ACN) with 1% trifluoracetic acid (TFA). The feed and displacer solution were prepared from the carrier solution. The feed consisted of 17 mg lysozyme and 5.35 mg of a pure recombinant growth factor protein. These conditions constitute high protein loading on the stationary phase.

The histogram shows a sharp boundary between the two zones corresponding to each of the proteins and between the zones containing the proteins and the displacer indicates an effective displacement. These sharp boundaries indicate that a successful separation resulted. The Raman spectra of the proteins purified by displacement were found to be identical to those of the respective proteins prior to displacement demonstrating the ability to purify proteins by displacement on RPLC supports without any protein denaturation.

Example 3

Figure 7:
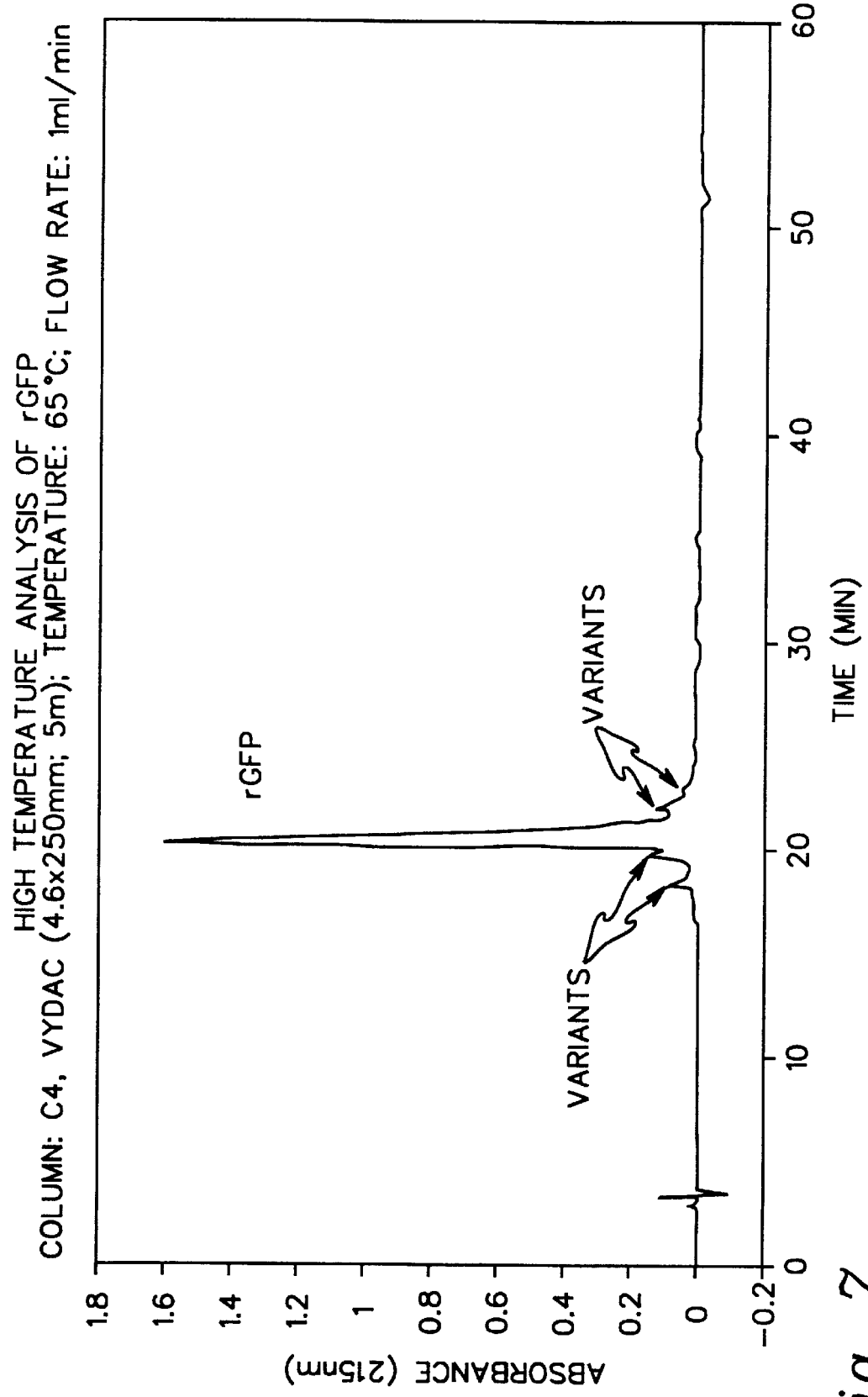
FIG. 7 is a high temperature reversed phase chromatogram of a growth factor protein feed stock showing variants closely associated with the main protein peak.

FIG. 7 shows a high temperature reversed phase chromatogram for a recombinant growth factor protein feed stock. Several peaks are closely associated with the main peak for the recombinant growth factor protein. These secondary peaks are for variants of the desired product differing by a single amino acid residue, and thus constitute a very difficult separation problem.

Figure 8:
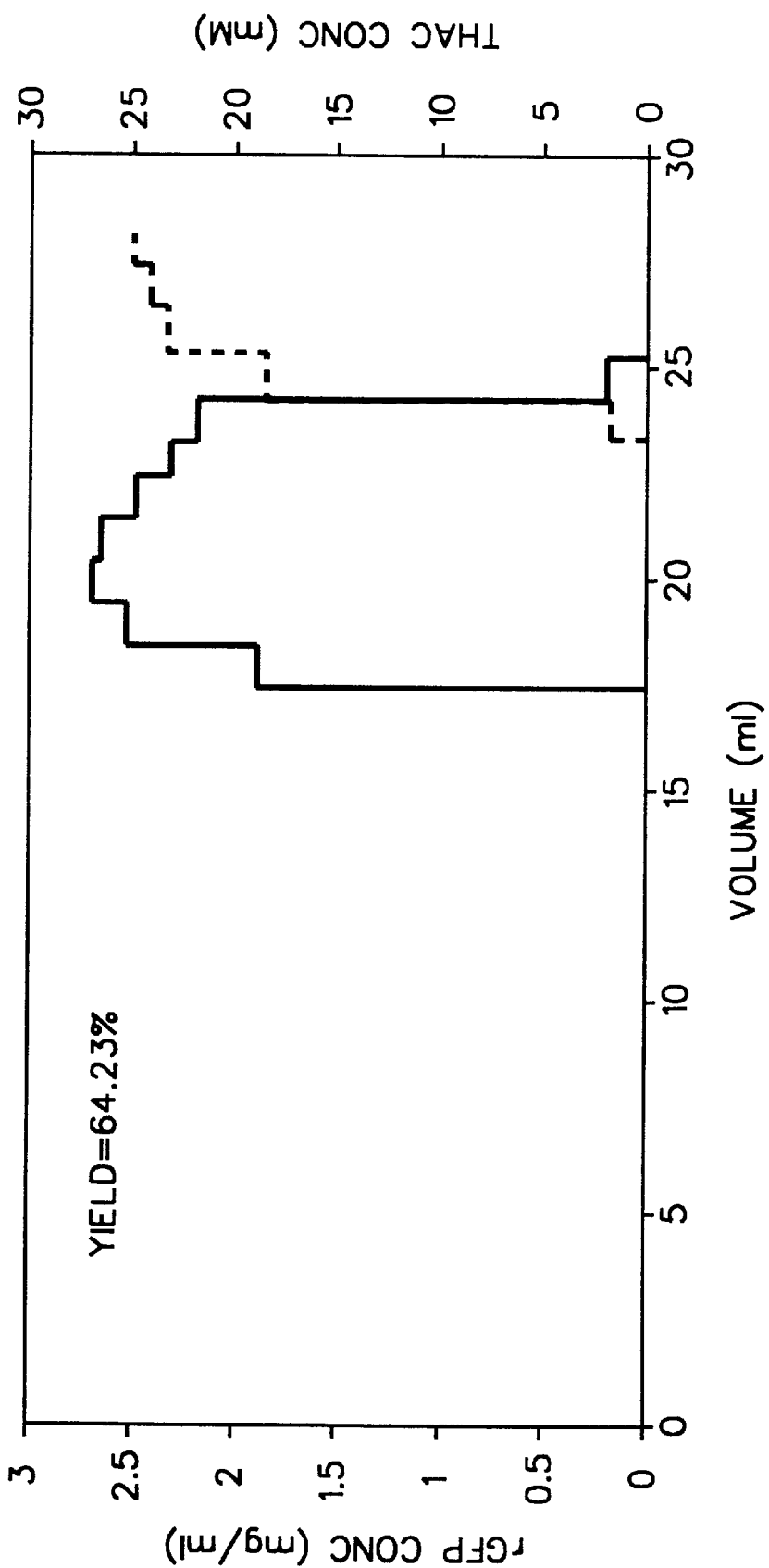
FIG. 8 is a displacement chromatogram for the growth factor protein feed stock shown in FIG. 7 that was purified on a reversed phase column using a low molecular weight, surface-active compound of the present invention.
Figure 9A:
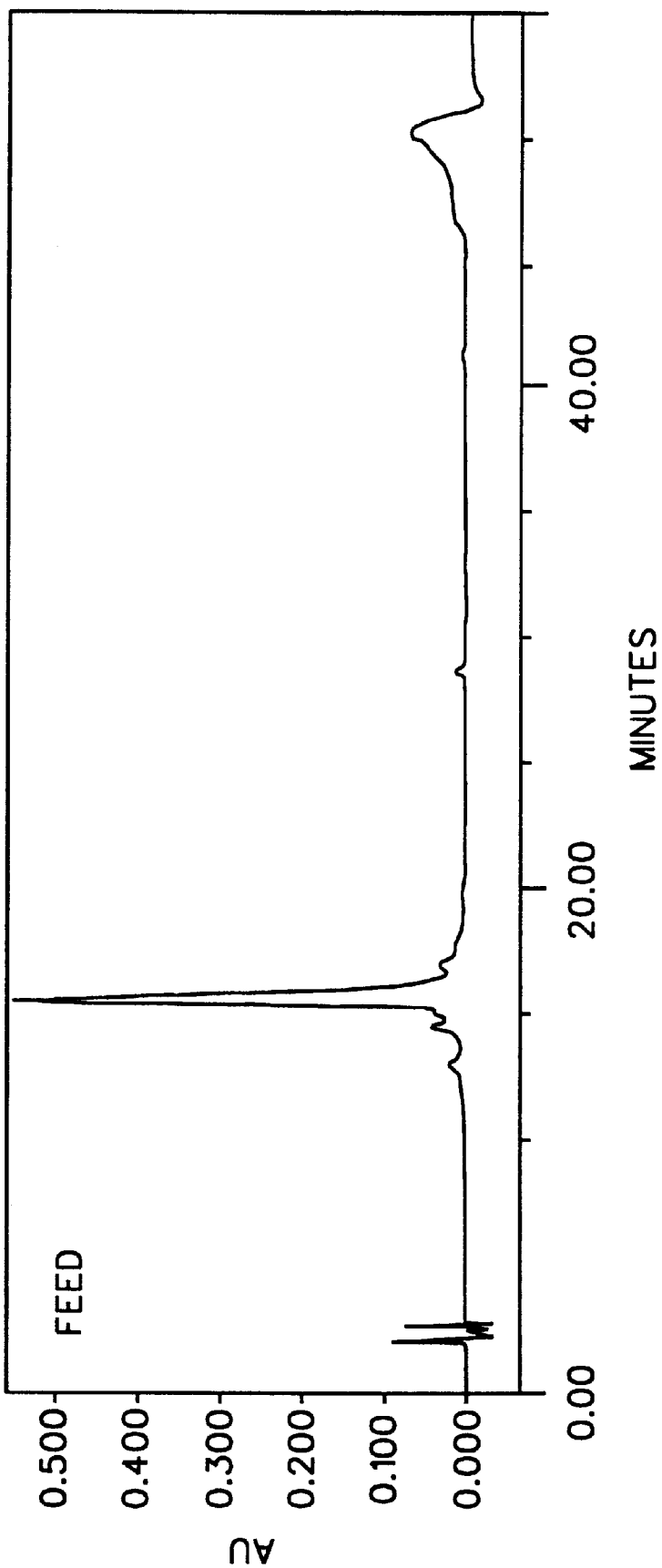
FIGS. 9 A–I show high temperature chromatograms of the growth factor feed stock and successive fractions from the displacement shown in FIG. 8.
Figure 9B:
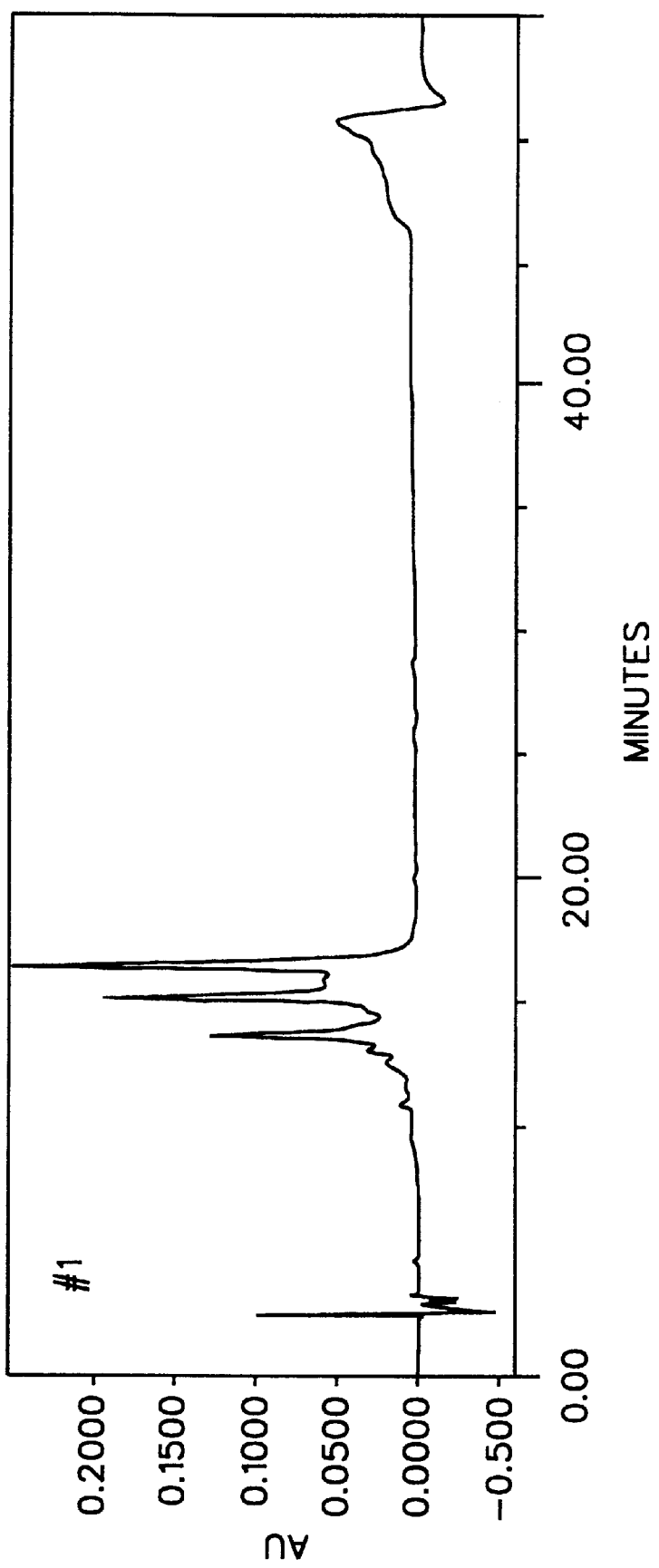
Figure 9C:
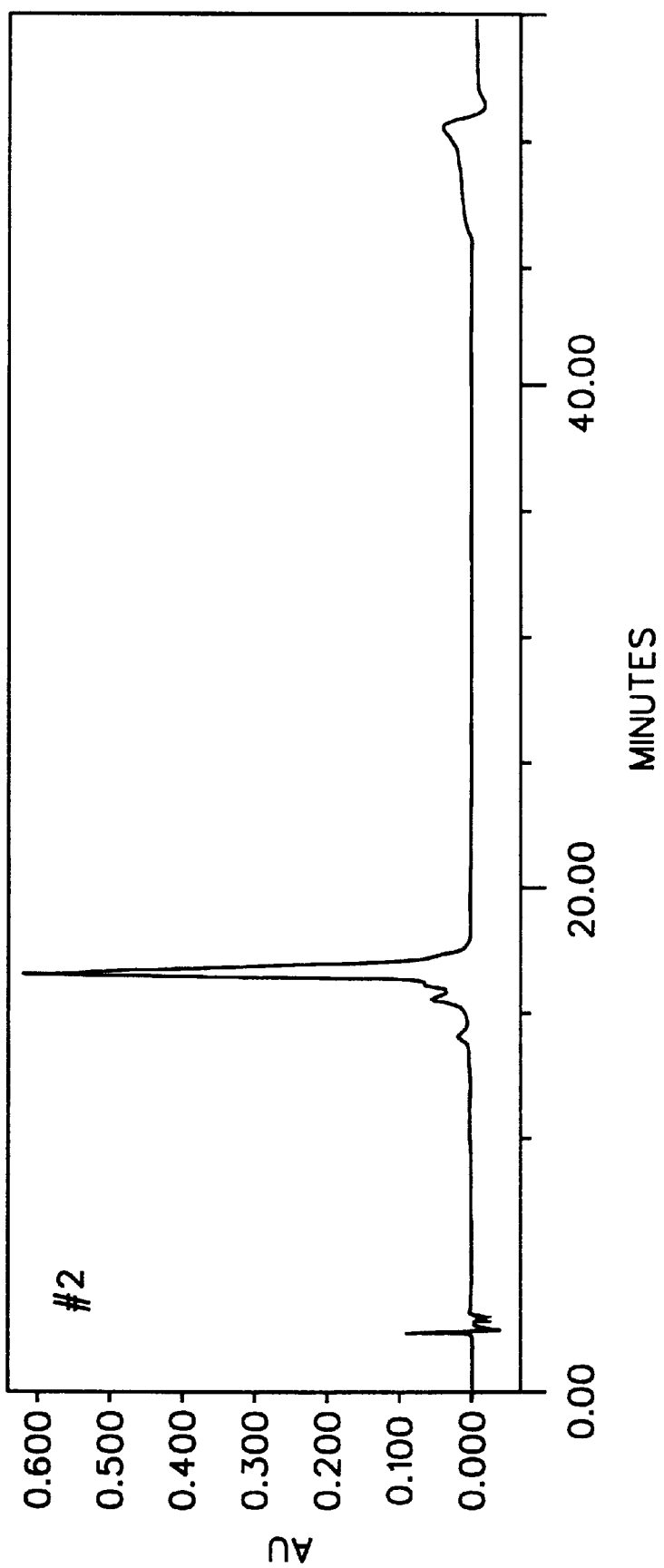
Figure 9D:
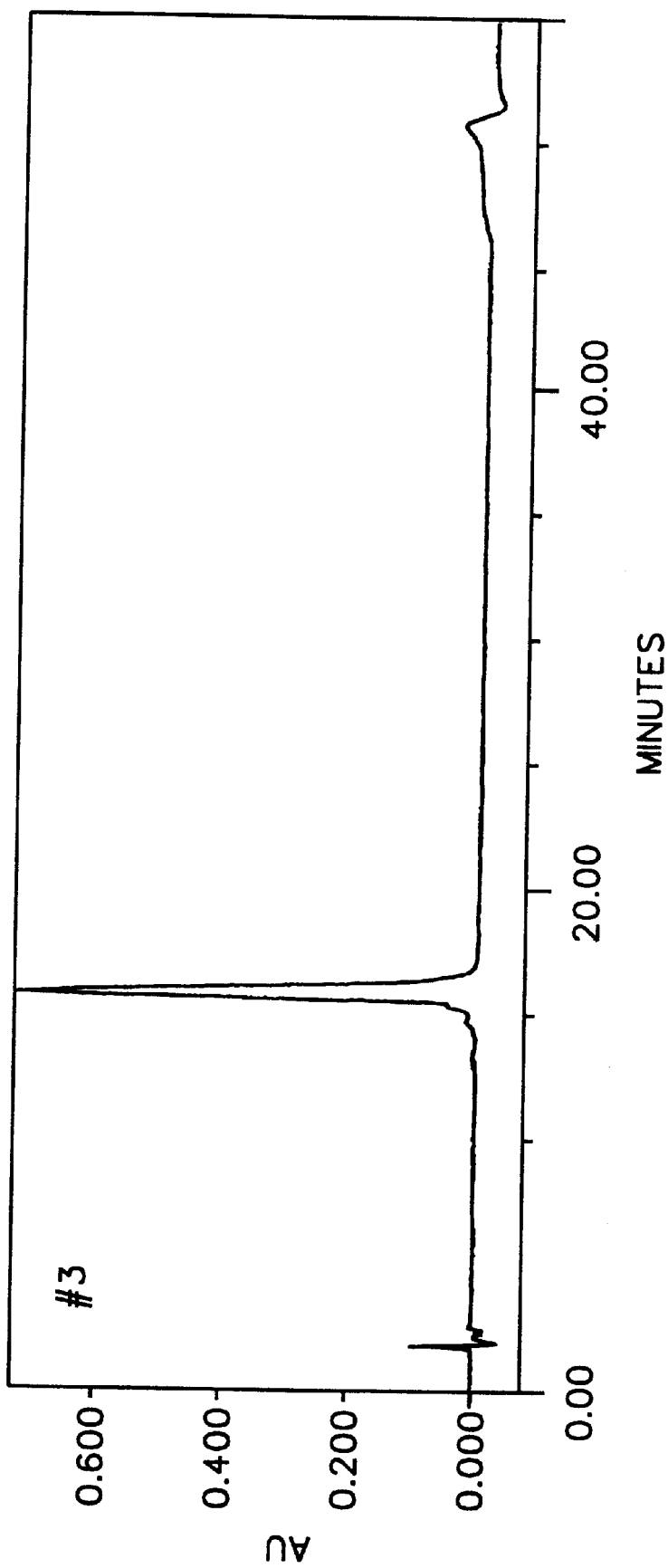
Figure 9E:
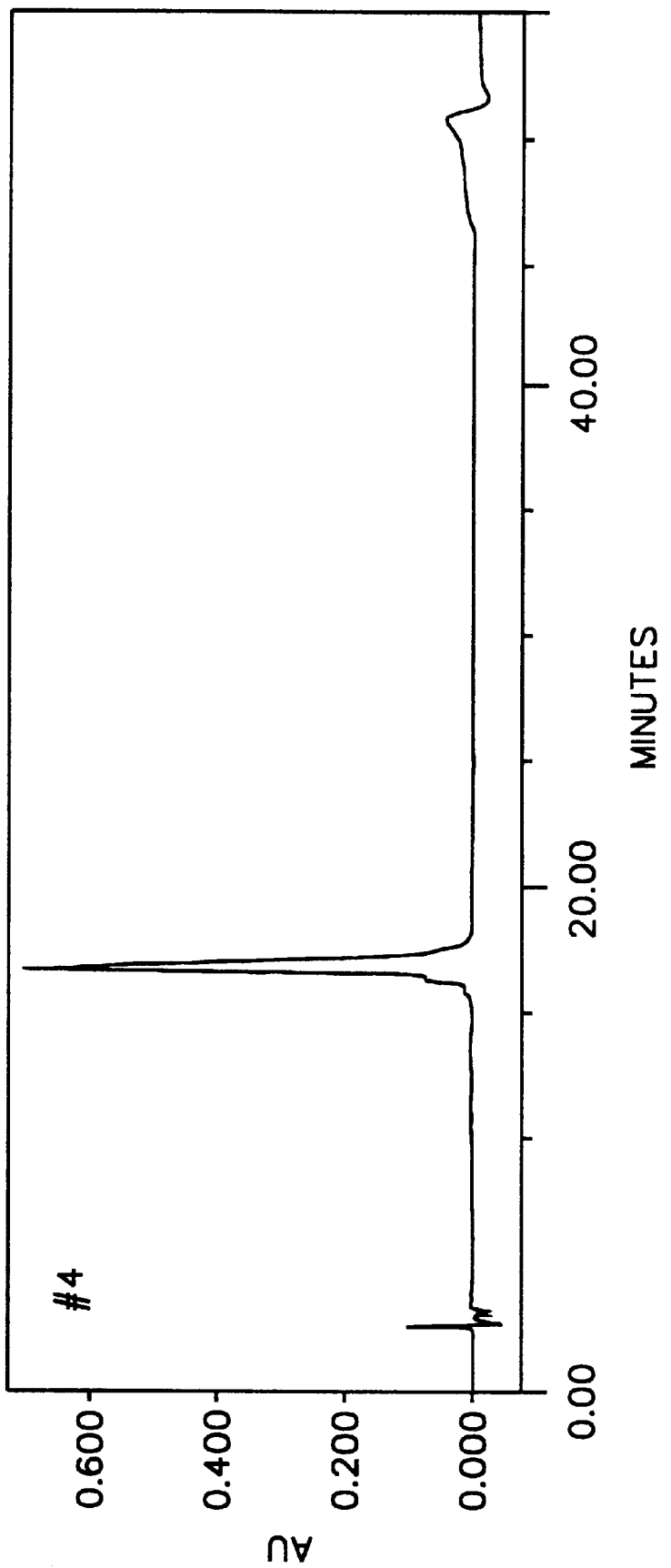
Figure 9F:
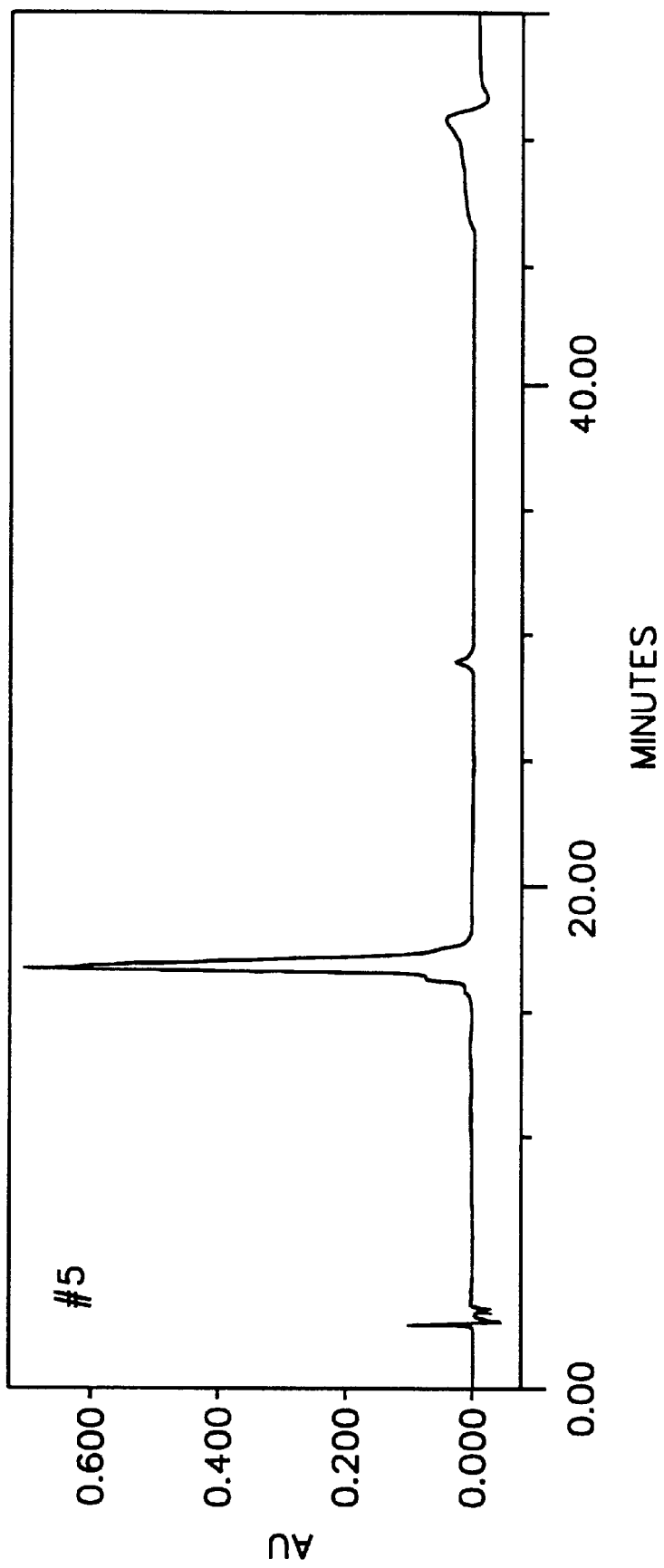
Figure 9G:
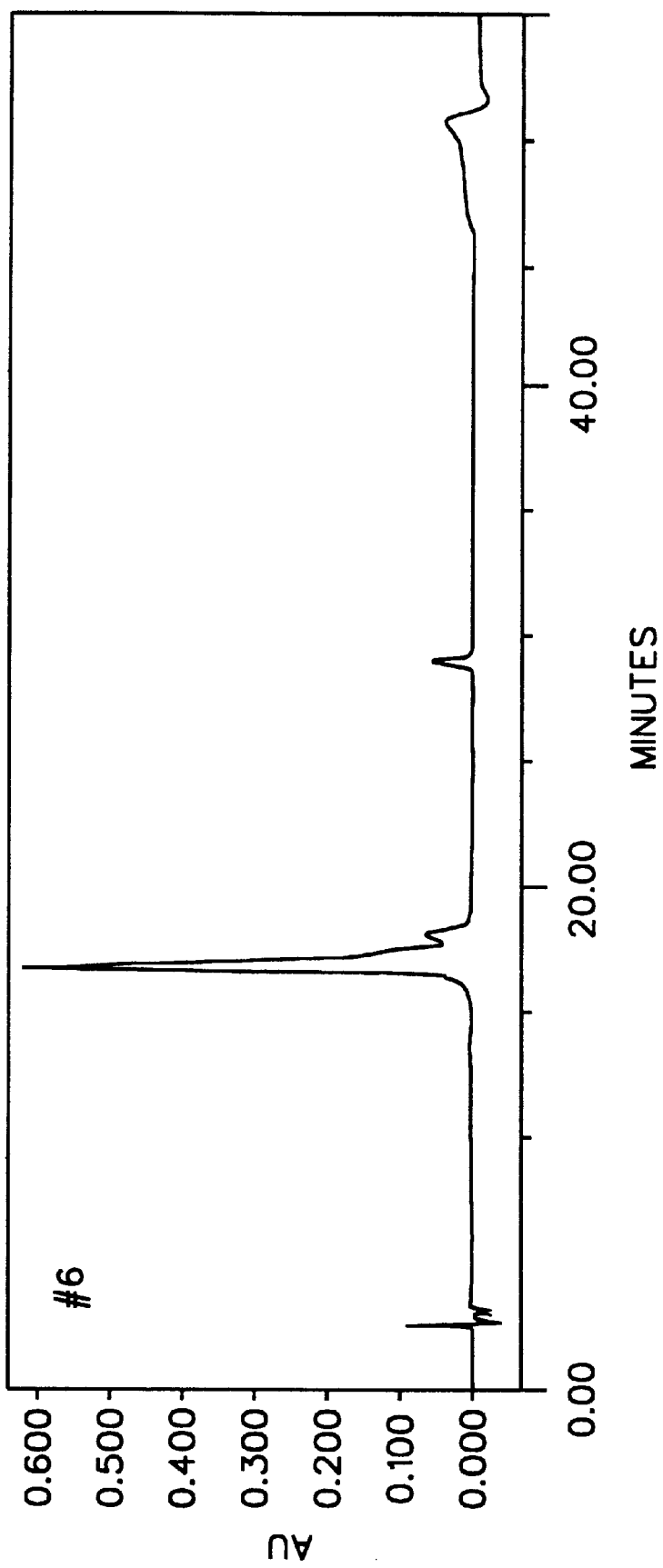
Figure 9H:
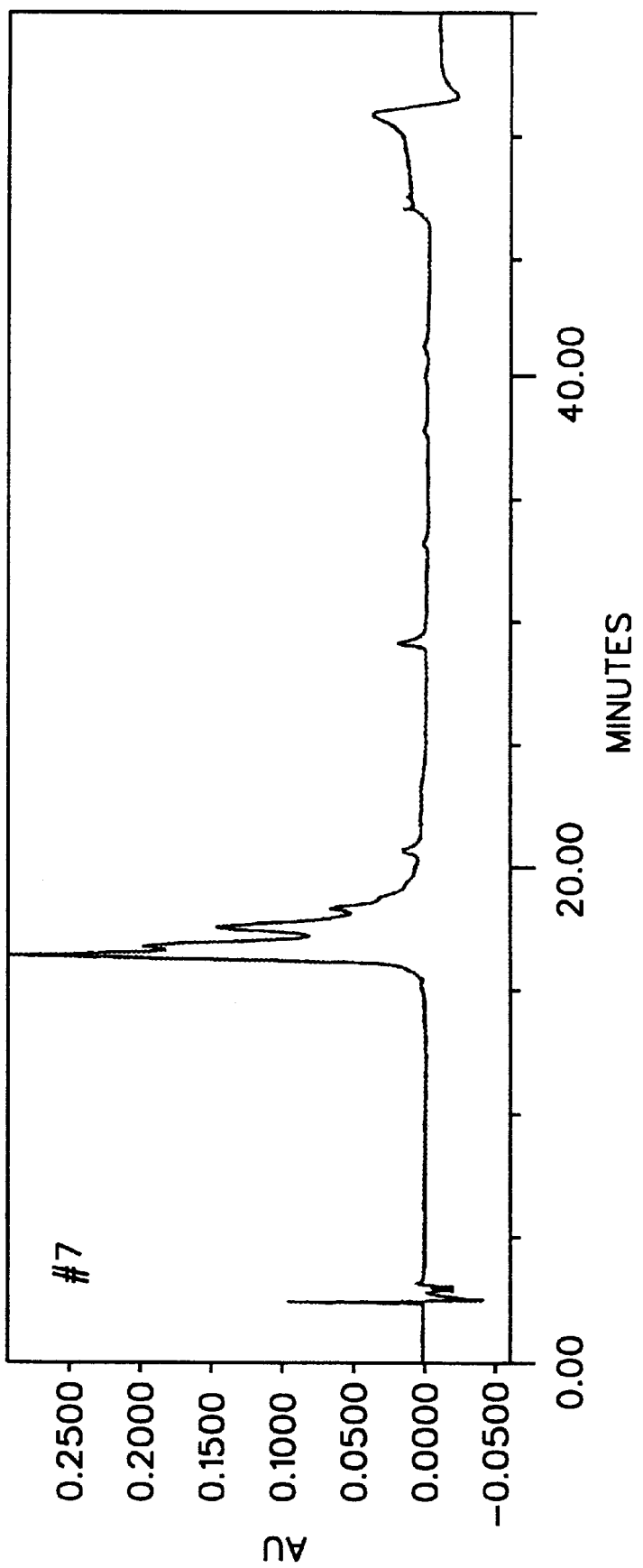
Figure 9I:
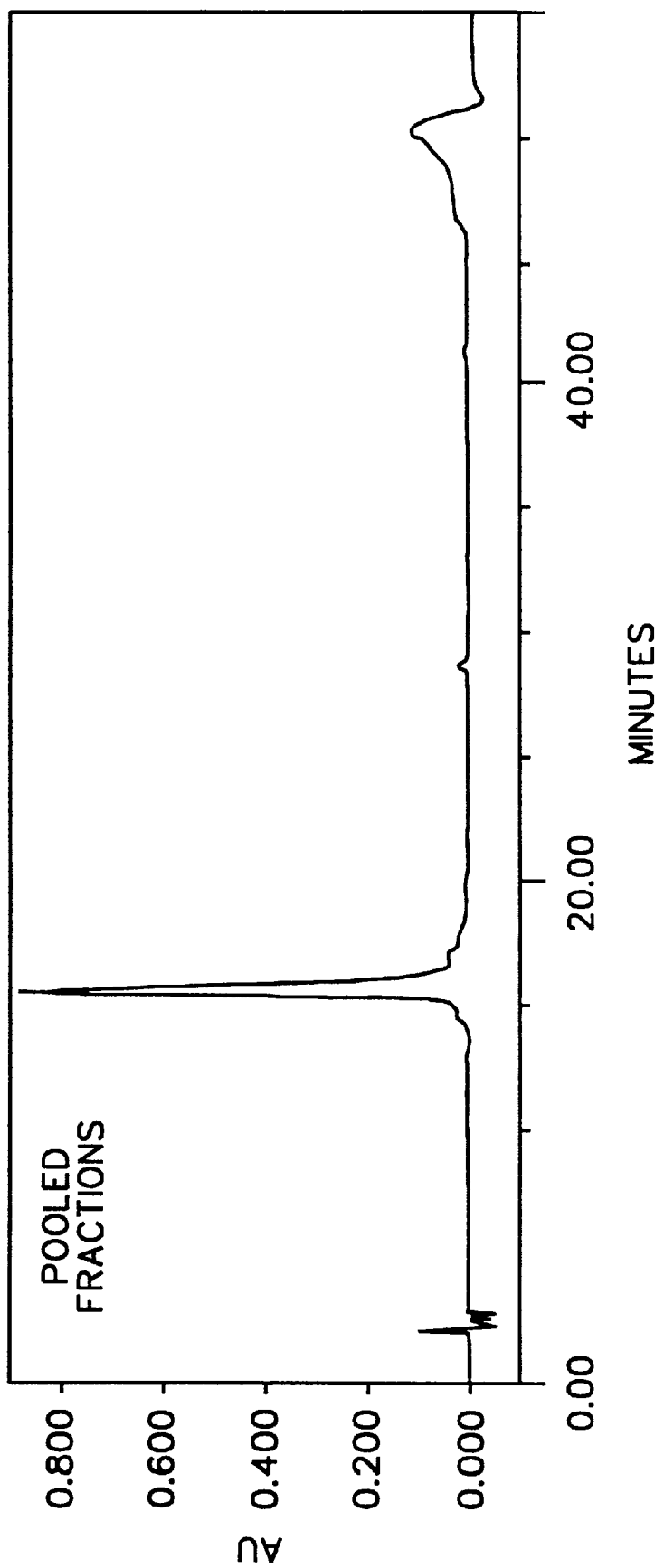

FIG. 8 shows the displacement of the recombinant growth factor protein feed stock described in FIG. 7 on a reversed phase chromatographic column using tetrahexylammonium chloride (THAC) as a displacer with a mobile phase composed of 16% acetonitrile and 0.15% trifluoracetic acid. A sharp drop in protein concentration was seen at the point when the displacer emerged from the column.

FIGS. 9A–I show the high temperature reversed phase assay for the feed stock and for the successive fractions from the displacement shown in FIG. 8. The first fraction from the zone of the displaced protein (#1) shows a higher concentration of the variants which elute before the main protein peak. The subsequent fractions (#3–#6) show purer product with the purity increasing to a level of over 97% in fraction #5. The fractions towards the end of the protein zone show higher concentrations of the variants that elute after the main protein on the high temperature assay. An overall yield of 64.2% at a purity of 96% was obtained for the recombinant growth factor protein. Thus, reversed phase displacement chromatography is able to resolve closely related protein variants from complex process streams that are typically encountered in bioprocessing.

Example 4

Figure 10:
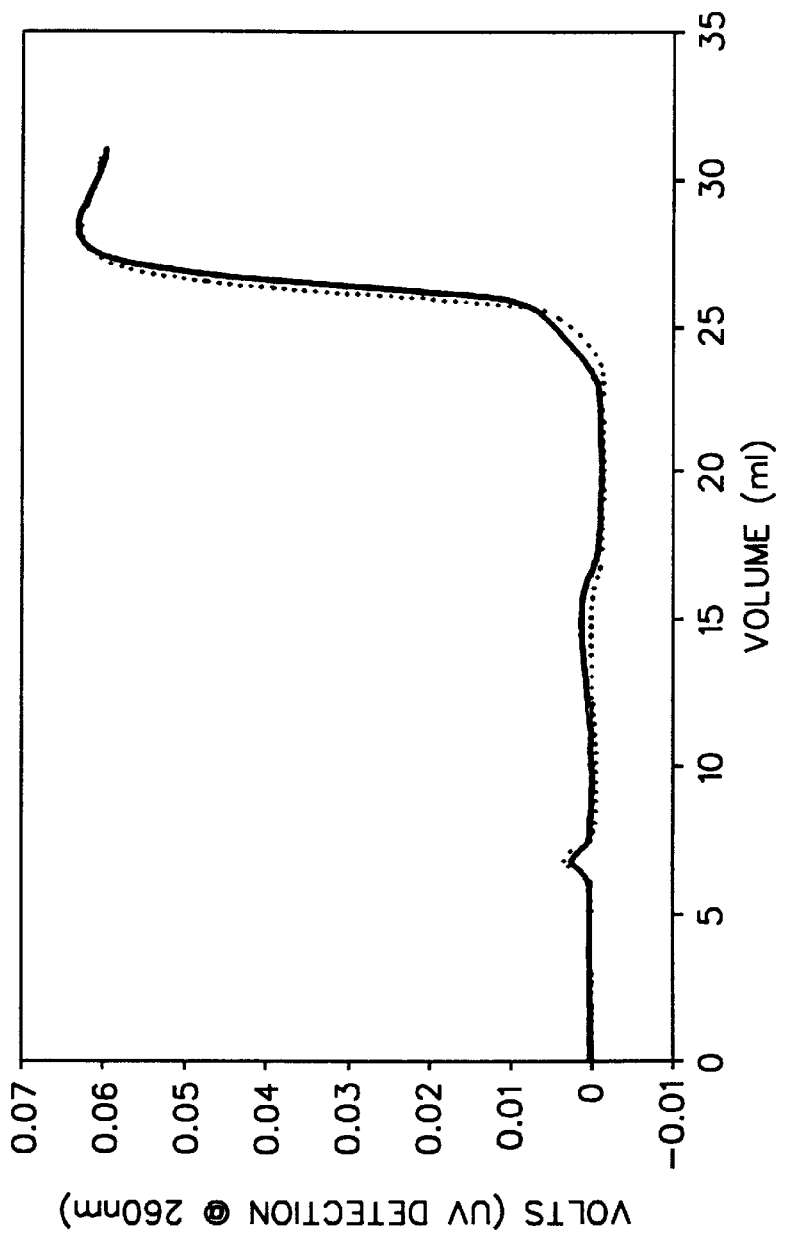
FIG. 10 is an overlay of the displacer breakthroughs in a HIC column before and after a displacement step using one of the displacers of the invention showing the effective regeneration of the column.

Demonstrating effective regeneration of the stationary phase after a series of displacement steps is important to enable the use of a compound as a displacer. FIG. 10 shows breakthrough curves for the displacer benzethonium chloride on a Phenyl 650M (Toso Haas) HIC stationary phase before and after the column had been put through several displacement and regeneration steps. As can be seen, the breakthrough curves almost overlay each other signifying an effective column regeneration using standard protocols.

While the invention has been particularly shown and described with reference to the preferred embodiments thereof, it will be understood by those skilled in the art that other changes in form and details may be made without departing from the spirit and scope of the invention.

What is claimed is:

1. A method for purifying a protein by displacement chromatography comprising:

(a) configuring a chromatographic system selected from the group consisting of hydrophobic interaction chromatography and reversed phase liquid chromatography, said chromatographic system having a hydrophobic stationary phase, for operation in displacement mode;

(b) selecting for use as a displacer a surface-active compound having molecular weight of less than 10,000 daltons and greater than 0 daltons and having a greater affinity for the hydrophobic stationary Phase than the protein;

(c) loading the protein on the hydrophobic stationary phase;

(d) displacing the protein from the stationary phase with said surface-active compound and moving the protein through the chromatographic system ahead of the displacer; and (e) collecting the displaced Protein.

2. The method of claim 1, wherein said chromatographic system is a hydrophobic interaction chromatographic system.

3. The method of claim 1, wherein said chromatographic system is a reversed phase liquid chromatographic system.

4. The method of claim 1, wherein said surface-active compound has one or more substituents selected from the group consisting of alkyl, substituted alkyl, aromatic and substituted aromatic.

5. The method of claim 1, wherein said surface-active compound is anionic.

6. The method of claim 1, wherein said surface-active compound is nonionic.

7. The method of claim 1, wherein said surface-active compound is cationic.

8. The method of claim 1, wherein said surface-active compound is selected from the group consisting of: alkylaryl sulfonates, alkylaryl sulfonic acids, diphenyl sulfonate derivatives, quaternary amines, sulfonates of benzene, sulfonates of cumene, sulfonates of toluene, sulfonates of xylene, sulfonates of condensed naphthalene, sulfonates of dodecylbenzenes, sulfonates of tridecylbenzenes, sulfonates of naphthalene, sulfonates of alkyl naphthalene, tridecyl benzene sulfonic acids and dodecyl benzene sulfonic acids.

9. The method of claim 1, wherein said surface-active compound has a molecular weight of less than 5,000 daltons.

10. The method of claim 9, wherein said chromatographic system is a hydrophobic interaction chromatographic system.

11. The method of claim 9, wherein said chromatographic system is a reversed phase liquid chromatographic system.

12. The method of claim 9, wherein said surface-active compound has one or more substituents selected from the group consisting of alkyl, substituted alkyl, aromatic and substituted aromatic.

13. The method of claim 9, wherein said surface-active compound is anionic.

14. The method of claim 9, wherein said surface-active compound is nonionic.

15. The method of claim 9, wherein said surface-active compound is cationic.

16. The method of claim 9, wherein said surface-active compound is selected from the group consisting of: alkylaryl sulfonates, alkylaryl sulfonic acids, diphenyl sulfonate derivatives, quaternary amines, sulfonates of benzene, sulfonates of cumene, sulfonates of toluene, sulfonates of xylene, sulfonates of condensed naphthalene, sulfonates of dodecylbenzenes, sulfonates of tridecylbenzenes, sulfonates of naphthalene, sulfonates of alkyl naphthalene, tridecyl benzene sulfonic acids and dodecyl benzene sulfonic acids.

17. The method of claim 9, wherein said surface-active compound has a molecular weight of less than 2000 daltons.

18. The method of claim 17, wherein said chromatographic system is a hydrophobic interaction chromatographic system.

19. The method of claim 17, wherein said chromatographic system is a reversed phase liquid chromatographic system.

20. The method of claim 17, wherein said surface-active compound has one or more substituents selected from the group consisting of alkyl, substituted alkyl, aromatic and substituted aromatic.

21. The method of claim 17, wherein said surface-active compound is anionic.

22. The method of claim 17, wherein said surface-active compound is nonionic.

23. The method of claim 17, wherein said surface-active compound is selected from the group consisting of: alkylaryl sulfonates, alkylaryl sulfonic acids, diphenyl sulfonate derivatives, quaternary amines, sulfonates of benzene, sulfonates of cumene, sulfonates of toluene, sulfonates of xylene, sulfonates of condensed naphthalene, sulfonates of dodecylbenzenes, sulfonates of tridecylbenzenes, sulfonates of naphthalene, sulfonates of alkyl naphthalene, tridecyl benzene sulfonic acids and dodecyl benzene sulfonic acids.

24. The method of claim 17, wherein said surface-active compound is cationic.

25. The method of claim 24, wherein said surface-active compound is benzethonium chloride.

26. The method of claim 24, wherein said surface-active compound is benzyltributylammonium chloride.

27. The method of claim 24, wherein said surface-active compound is tetrahexylammonium chloride.

28. The method of claim 24, wherein said surface-active compound is rhodamine.

29. A method for purifying a protein by displacement chromatography comprising:

(a) configuring a chromatographic system selected from the group consisting of hydrophobic interaction chromatography and reversed phase liquid chromatography, said chromatographic system having a hydrophobic stationary phase for operation in displacement mode;

(b) selecting from the group consisting of benzethonium chloride, benzyltributylammonium chloride, tetrahexylammonium chloride and rhodamine, a surface-active compound for use as a displacer, said surface-active compound having a greater affinity for the hydrophobic stationary phase than the protein;

(c) loading the protein on the hydrophobic stationary phase;

(d) displacing the protein from the stationary phase with said surface-active compound and moving the protein through the chromatographic system ahead of the displacer; and (e) collecting the displaced protein.

30. The method of claim 29 wherein said chromatographic system is hydrophobic interaction chromatography.

31. The method of claim 29 wherein said chromatographic system is reversed phase liquid chromatography.

* * * * *